United States Patent [19]
Fugedi et al.

[11] Patent Number: 5,739,115
[45] Date of Patent: Apr. 14, 1998

[54] SULFATED MALTOOLIGOSACCHARIDES WITH HEPARIN-LIKE PROPERTIES

[75] Inventors: Peter Fugedi; David J. Tyrrell, both of Alameda; Robert J. Tressler, Moss Beach; Robert J. Stack, Murphys, all of Calif.; Masayuki Ishihara, Tokyo, Japan

[73] Assignee: Glycomed Incorporated, Alameda, Calif.

[21] Appl. No.: 312,571

[22] Filed: Sep. 26, 1994

Related U.S. Application Data

[63] Continuation-in-part of Ser. No. 133,483, Oct. 7, 1993, abandoned.

[51] Int. Cl.⁶ .......................... A61K 31/70; C07H 15/00
[52] U.S. Cl. ........................ 514/24; 514/23; 514/25; 514/53; 514/54; 514/61; 514/824; 536/4.1; 536/59; 536/109; 536/118
[58] Field of Search .................. 536/4.1, 59, 109, 536/118; 514/23, 24, 25, 53, 54, 61, 824

[56] References Cited

U.S. PATENT DOCUMENTS

| | | | |
|---|---|---|---|
| 4,021,544 | 5/1977 | Nair et al. | 514/54 |
| 5,380,747 | 1/1995 | Medford et al. | 514/423 |

FOREIGN PATENT DOCUMENTS

| | | | |
|---|---|---|---|
| 0 338 092 | 10/1989 | European Pat. Off. | |
| A 60-174729 | 9/1985 | Japan | A61K 47/00 |
| 5 139 980 | 6/1993 | Japan | |
| WO 88/05301 | 7/1988 | WIPO | A61K 31/725 |
| 8 903 684 | 5/1989 | WIPO | |

OTHER PUBLICATIONS

Naito et al., "*In vivo* selection of human renal cell carcinoma cells with high metastic potential in nude mice," Clin. Expl. Metastatic (1989) 7:4:381–389.

Naito et al., "Evidence for Metastatic Heterogeneity of Human Renal Cell Carcinoma," Anticancer Research (1988) 8:1163–1168.

Fugedi et al. XVIth International CarbohydrateSymposium, Jul. 5–10th, 1992, Paris, France, p. 402, abstract No. B069.

Fugedi et al. XVIth International CarbohydrateSymposium, Jul. 5–10th, 1992, Paris, France, p. 446, abstract No. B113.

*Primary Examiner*—Kathleen K. Fonda
*Attorney, Agent, or Firm*—Lyon & Lyon LLP

[57] ABSTRACT

A novel class of highly sulfated maltooligosaccharide having heparin-like activity is described, as well as methods for using these oligosaccharides to treat certain diseases including cancer, and retinopathies.

10 Claims, 9 Drawing Sheets

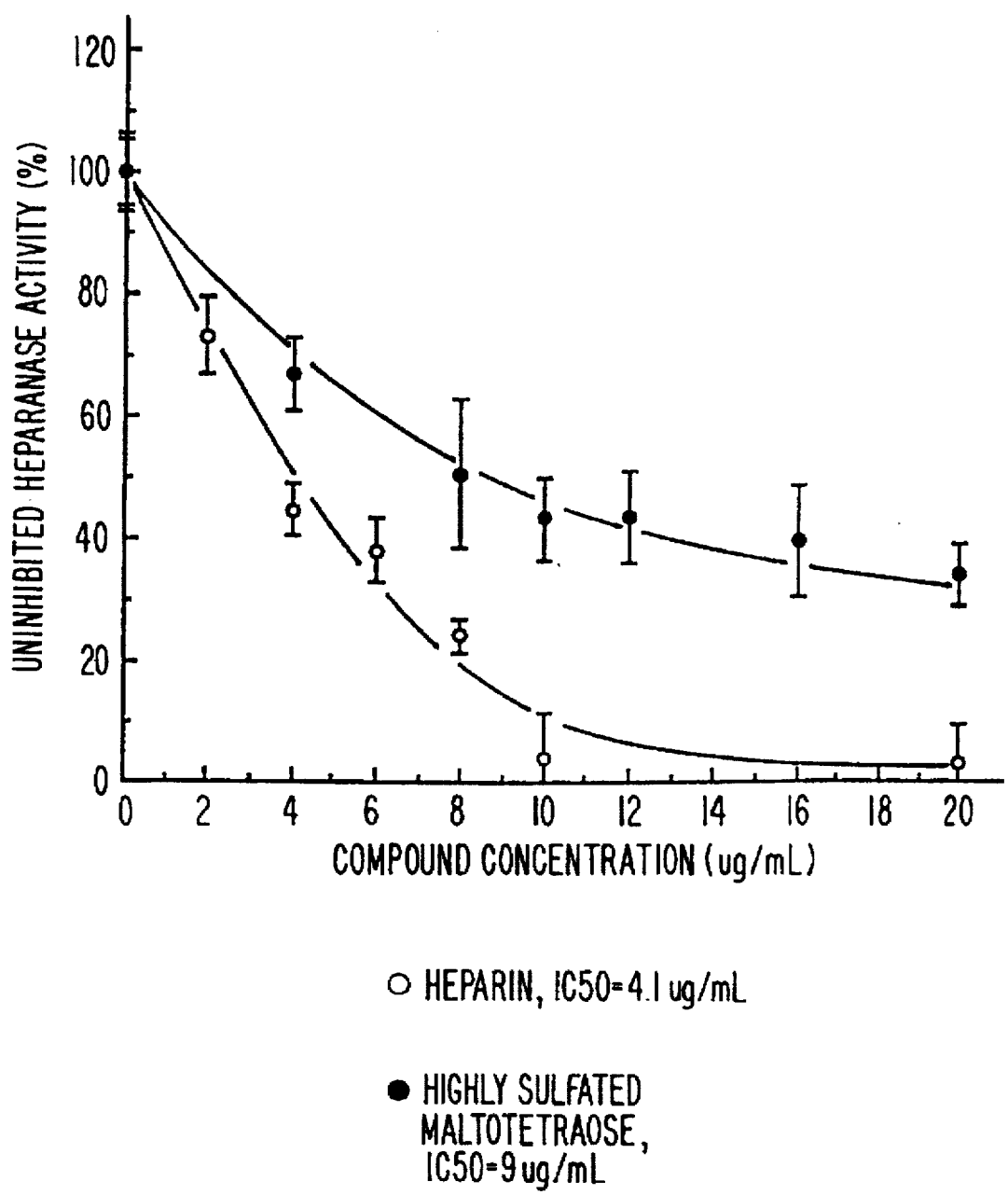

SULFATED MALTOOLIGOSACCHARIDES WITH HEPARIN-LIKE PROPERTIES

FIELD OF THE INVENTION

This application is a continuation-in-part of U.S. application Ser. No. 08/133,483, filed on Oct. 7, 1993, now abandoned. The invention relates to a novel class of highly sulfated maltooligosaccharides having heparin-like activity, and to methods for using these oligosaccharides, alone or in combination with a chemotherapeutic drug, to treat certain diseases.

BACKGROUND OF THE INVENTION

Heparin and other naturally occurring glycosaminoglycans, such as dermatan sulfate or heparan sulfate, possess medically useful properties. Recently, several low molecular weight heparins from various chemical or enzymatic alepolymerization processes have been developed for clinical use. Thomas et al., *Thrombos. Res.* (1982) 28:343-350; Walenga et al., *Thrombos. Res.* (1986) 43:243-248; Koller et al., *Thrombos Haemostas*, (1986) 56:243-246. For instance, the involvement of heparin or heparan sulfate or degradation products thereof in smooth muscle proliferation has been recognized for some time. Heparin and heparan sulfate can slow or arrest the vascular proliferation associated with injury described hereinabove (Clowes, A. W., et al., *Nature* (1977) 265:625-626). The effect of heparan sulfate and heparin on smooth muscle proliferation is also described by Marcum, J. A., et al. in *Biology of Proteoglycan*, Academic Press (1987) pp. 301-343. The inhibition of vascular smooth muscle cell growth by heparin was further described by Casteliot, J. J., Jr., et al., *J. Biol Chem* (1982) 257:11256-11260, and the effect of heparin on vascular smooth muscle cell growth in fetal tissue was described by Benitz, W. E., et al., *J. Cell Physiol* (1986) 127: 1-7. The effect of heparin as an inhibitor of both pericyte and smooth muscle cell proliferation was shown by Orlidge, A., et al., *Microvascular Research* (1986) 31:41-53, and these authors further showed that chondroitin sulfate, and dermatan sulfate do not have this effect. A review of the effects of heparin and heparan sulfate on the proliferation of smooth muscle cells has been published by Benitz, W. E. in "The Pulmonary Circulation: Normal and Abnormal", Fishman, A. P., ed., University of Pennsylvania Press (1988).

Heparins and certain low molecular weight heparins have certain disadvantages for medical applications. Generally, both compositions exhibit anticoagulant activity, and thus must be administered with considerable medical supervision. Recently, however, non-anticoagulant heparins have been developed to circumvent this problem and are now undergoing clinical trials. Secondly, heparins are of natural origin, generally being purified from animals. As such, small amounts of the glycosaminoglycans may cause anaphylactic reactions, a decrease in the number of thrombocytes, thrombosis and embolism. Therefore, the preparation or identification of synthetic agents possessing properties comparable to heparin is desired.

Biologically active hexose polymers or modified heparins have been described previously that display certain heparin properties. U.S. Pat. No. 4,066,829 discloses complement system-modulating activity for sulfated maltodextrin polymers of undisclosed molecular weight. Similar complement system-modulating activity for 4-O-polyhexose-thioarylene sulfate derivatives is disclosed in U.S. Pat. No. 4,470,976 and U.S. Pat. No. 4,435,387. The hexose polymers described are substituted disaccharides.

EPA 0338092 describes alkali metal or alkaline earth metal salts of a sulfated linear polymer of 4 to 10 D-glucose units linked $\alpha$-1,4. These compositions are claimed to have anti-HIV activity.

PCT patent application, WO 92/01003, shows that certain non-anticoagulant heparins act as heparanase inhibitors, and that they may be effective in lessening or preventing lung colonization by metastatic cell variants. Two scientific abstracts by Fugedi et al describe sulfated maltooligosaccharides. See, XVIth International Carbohydrate Symposium, July 5-10th, 1992, Paris-France: Modulation of bFGF Biological Activities by Sulfated Maltooligosaccharides, page 402; and Antiviral Activity of Sulfated Maltooligosaccharides, page 446. That these compositions can bind basic fibroblast growth factor and inhibit herpes simplex virus plaque formation is also described. However, there is no description of the extent of sulfation of these compositions, and what effect high levels of sulfation would have on biological activity.

SUMMARY OF THE INVENTION

The instant invention provides highly sulfated maltooligosaccharide compositions having therapeutic and/or prophylactic properties alone or in combination with a chemotherapeutic drug. In certain respects the compositions have properties similar to heparin.

In another respect the invention provides highly sulfated maltooligosaccharide compositions that are effective inhibitors of smooth muscle cell proliferation.

A third aspect of the invention is the description of highly sulfated maltooligosaccharide compositions that have the following structural formula:

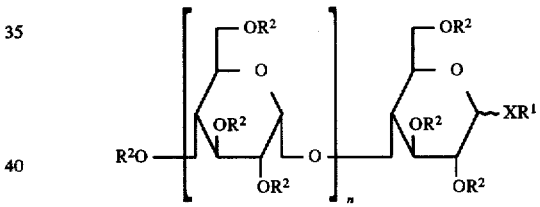

where

X represents O or S;

each $R^1$ independently represents an alkyl, aryl, or aralkyl group, a reduced or oxidized glucose unit, $SO_3M$, or H;

$R^2$ represents a $SO_3M$ group or H;

M represents a biologically acceptable cation; and n represents an integer from 1 to 9;

with the proviso that at least 50% of $R^2$ groups are $SO_3M$.

A fourth aspect of the invention is the description of preferred highly sulfated maltooligosaccharide compositions including sulfated maltotetraose, sulfated maltopentaose, and sulfated maltohexaose.

A fifth aspect of the invention is the description of sulfated maltooligosaccharide compositions that differentially affect cell proliferation depending on the degree of sulfation of the compositions.

A sixth aspect of the invention is the description of highly sulfated maltooligosaccharide compositions that can be beneficially applied to the treatment or prevention of certain diseases including cancer, cardiovascular disease, retinopathies, inflammation, and diseases of viral origin.

These and other aspects of the invention will become apparent to a practitioner of this art upon a full consideration of the disclosure presented below.

BRIEF DESCRIPTION OF THE DRAWINGS

FIG. 11 shows the effects of highly suffated maltotetraose on heparanase inhibition.

DESCRIPTION OF SPECIFIC EMBODIMENTS

Figure 1:
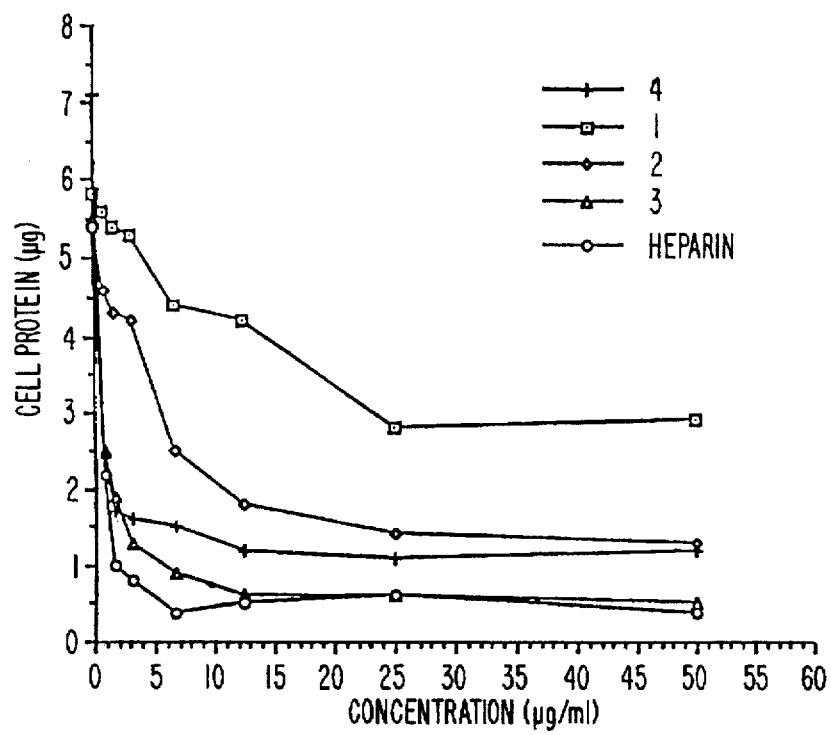
FIG. 1 shows the effects of the degree of sulfation of certain maltooligosaccharides on binding of RO-12 UC cells to bFGF coated microtiter wells.

All publications and patent applications discussed or cited herein are understood to be incorporated by reference to the same extent as if each individual publication or patent application was specifically and individually set forth in its entirety.

The instant invention provides compositions having therapeutic properties similar to heparin. The compositions of the instant invention are highly sulfated maltooligosaccharides having the general structure given by the formula:

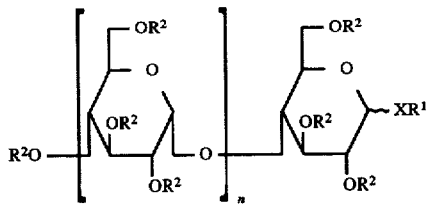

where

X represents O or S;

each R1 independently represents an alkyl, aryl or aralkyl group, a reduced or oxidized glucose unit, $SO_3M$ or H;

$R^2$ represents a $SO_3M$ group or H;

M represents a biologically acceptable cation; and n represents an integer from 1 to 9;

with the proviso that at least 50% of $R^2$ are $SO_3M$.

Typical examples of biologically acceptable cations are alkali metals, alkaline earth metals, aluminum, ammonia, zinc, and substituted ammonia wherein the substitution may produce a di- or trialkylamine $(C_1-C_6)$, piperidine, pyrazone, alkanolamine $(C_2-C_6)$, or cycloalkylamine $(C_3-C_6)$, although acceptable cations are not limited to these. Any cation providing reasonable solubility and low or no toxicity and which does not significantly, or adversely affect the pharmaceutical properties of the parent composition is acceptable.

Preferred highly sulfated compositions of the instant invention are maltotetraose, maltopentaose, maltohexaose, maltoheptaose, maltooctaose, maltononaose and maltodecaose.

The compositions of the invention can be made by treating a maltooligosaccharide, or a derivative thereof as described below, with a sulfating agent in an appropriate solvent by methods which are well known in the art. Maltooligosaccharide stag materials for the synthesis of the compositions of the instant invention include oligosaccharides having 1 to 9 D-glucose residues linked α-1,4 or mixtures of these oligosaccharides. Derivatives of these oligosaccharides, such as O- or S-glycosides or reduced alditol derivatives, are useful as starting material as well. It will be apparent that the structure of the final sulfated oligosaccharide desired will determine the nature of the starting material.

Sulfating agents useful in preparing the compositions of the instant invention include but are not limited to sulfur trioxide:pyridine complex, sulfur trioxide:trirnethylamine complex, and chlorosulfonic acid. Organic solvents useful for the preparation of the compositions of the instant invention include but are not limited to N,N-dimethylformamide (DMF), dimethylsulfoxide, and pyridine. Using techniques known in the art, selective sulfation of the hydroxyl groups can be obtained. After sulfation, the sulfate groups can be modified to possess biologically acceptable cations, including but not limited to Na, K, Li, Ca, Mg, $NH_4$, Al, ethanolmine, triethanolamine, morpholine, pyridine and pipeidine.

A typical sulfation reaction is carded out by dissolving the starting material (0.5 g) in N,N-dimethylformamide (20 mL) and adding sulfur trioxide pyridine complex (2 equivalents/ OH groups). The mixture is stirred at room temperature for an appropriate time, preferably 2 days. The pH is adjusted to 9 by the addition of 1M NaOH, then the crude product is either precipitated by the addition of an organic solvent (as e.g. ethanoD, or if this is not appropriate the mixture is evaporated to dryness under reduced pressure. The crude product is then purified to remove inorganic salts, and finally converted into the desked salt form.

An important aspect of the instant invention is the sulfate content of the products. The products are characterized as the sulfur content determined by elementary analysis. Because of the hygroscopic nature of the sulfated compositions this cannot be regarded as a reliable method, therefore in the present work the sulfate content was determined from the carbon/sulfur ratio which is independent from the moisture content of the samples. The sulfate content of the products can be expressed as the sulfation ratio, which is the ratio of the number of sulfated hydroxyl groups to the total number of hydroxyl groups in the starting material, expressed as percentage.

Depending on the specific sulfation method employed, the sulfate esters prepared will vary in the number and position of sulfonic acid substituents. In most cases, a mixture of sulfate esters of the starting oligosaccharide(s) will be obtained. Preferred compositions have about 50% of the hydroxyl groups sulfated. More preferred are compositions having 75% or greater of the hydroxyl groups sulfated.

Mixtures of different maltooligosaccharides may be sulfated and utilized for medical applications. For example, a maltooligomer mixture is commercially available which includes linear homologs from the tetrasaccharide to the decasaccharide. Such a mixture was highly sulfated using the conditions described herein (0.25 g maltooligomer mixture in 10 ml DMF treated with sulfur trioxide pyridine complex).

Labeled Forms of the Invention Non-Anticoagulant Compositions

The compositions of the invention can be provided with fluorescent, radioisotope, or enzyme labels as desired. Conventional techniques for coupling of label to carbohydrates or related moieties can be used. Such techniques are well established in the art. See, for example, U.S. Pat. No. 4,613,665. The labeled mixtures of the invention may be used to identify sites of disease as well as in competitive immunoassays, and as a means to trace the pharmacokinetics of the compositions in vivo. Suitable radioisotope labels for this purpose include hydrogen$^3$, iodine$^{131}$, indium$^{111}$, technetium$^{99}$, phosphorus$^{32}$, and sulphate$^{35}$. Suitable enzymic labels include alkaline phosphatase, glucose-6-phosphate-dehydrogenase, and horseradish peroxidase. Particularly preferred fluorescent labels include fluorescein and dansyl. A wide variety of labels of all three types is known in the art.

Administration and Use

The compositions of the instant invention are useful in medical applications for treating or preventing a variety of diseases including cancer, preferably metastatic cancer, inflammation, and diseases caused or exacerbated by platelet aggregation, or anglogenesis, and for the treatment of conditions or diseases which are characterized by excessive and destructive smooth muscle cell proliferation.

The instant compositions, because of their angiostatic activity, will be preferably applied for the beneficial treatment of angiogenic-based diseases. One such class of diseases is cancer or retinopathies. A member of this latter class is diabetic retinopathy that will be favorably treated by the compositions of the instant invention.

Administration of the compositions of the invention is typically by routes appropriate for glycosaminoglycan compositions, and generally includes systemic administration, such as by injection.

Particularly preferred is subcutaneous injection, as continuous injection over long time periods can be easily continued. Also preferred are introduction into the vascular system through intraluminal administration or by adventitial administration using osmotic pumps or implants. Typical implants contain biodegradable materials such as collagen, polylactate, polylactate/polyglycoside mixtures, and the like. These may be formulated as patches or beads. Typical dosages are in the range of 0.1–100 mg/kg/day on a constant basis over a period of 5–30 days. A particularly preferred dosage is about 0.3 mg/kg/hr, or, for a 70 kg adult, 21 mg/hr or about 500 mg/day. For certain applications, including cancer, the doses and periods of treatment will be chosen by the physician that best fit the need of the patient.

Other modes of administration are less preferred but maybe more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable compendium of formulations is found in *Remington's Pharmaceutical Sciences*, Mack Publishing Company, Easton, Pa., latest edition.

The compositions of the invention may also be labeled using typical methods such as radiolabeling, fluorescent labeling, chromophores or enzymes, and used to assay the amount of such compositions in a biological sample following its administration. Suitable protocols for competitive assays of antlyres in biological samples are well known in the art, and generally involve treatment of the sample, in admixture with the labeled competitor, with a specific binding panner which is reactive with the analyte such as, typically, an immunoglobulin or fragment thereof. The antibodies prepared according to the invention, as described below, are useful for this purpose. The binding of analyte and competitor to the antibody can be measured by removing the bound complex and asstying either the complex or the supernatant for the label. The separation can be made more facile by preliminary conjugation of the specific binding parmer to a solid support. Such techniques are well known in the art, and the protocols available for such competitive assays are too numerous and too well known to be set forth in detail here.

As referred to above, the oligosaccharide compositions of the invention are useful in therapeutic applications for the treatment of conditions or diseases which are characterized by excessive and destructive smooth muscle cell proliferation. These conditions frequently occur where the subject has been exposed to trauma, such as in the case of surgical patients. The trauma caused by wounds or surgery results in vascular damage and secondary smooth muscle cell proliferation, which results in vascular restenosis. This undesirable result can occur after vascular graft surgery, heart transplantation, balloon or laser angioplasty, arterial traumatic injury, postsurgical repair of muscular arteries, long-term in-dwelling of arterial catheters, invasive arterial diagnostic procedures, kidney, lung or liver transplants, coronary artery bypass surgery, carotid artery bypass surgery, femoral popliteal bypass surgery, and intracranial arterial bypass surgery.

In addition to secondary smooth muscle cell proliferation events occurring as a result of trauma, certain diseases are associated with unwanted vascular proliferation, although in these cases, too, it is assumed that some internal unknown injury has caused the secondary result. These disease states include Goodpasture syndrome, acute glomerulonephritis, neonatal pulmonary hypertension, asthma, congestive heart failure, adult pulmonary hypertension, and renal vascular hypertension.

The compositions of the instant invention are useful as inhibitors of smooth muscle cell proliferation, a preferred application is the inhibition of the proliferation of smooth muscle cells in blood vessel walls that occurs in response to vascular injury, and in association with certain disease states (Austin, G. E., et at., *J Am Coll Cardiol* (1985) 6:369–375). The proliferation of these cells can have negative effects due to the production of excess proteins or other matrix molecules, which, along with the cells themselves, form pathologic lesions of, for example, atherosclerosis, renal hypertension, pulmonary hypertension, vasculitis, and post-surgical vascular restenosis. These results are distinguished from the acute response to trauma characterized by blood clotting.

In certain of the experiments described herein, the invention compositions were compared to porcine mucosal heparin. Suitable procedures for the preparation of the heparin starting material are found, for example, in Charles, A. F., et at., *Biochem J* (1936) 30: 1927–1933, and modifications of this basic procedure are also known, such as those disclosed by Coyne, E., in *Chemistry and Biology of Heperin*, Elsevier Publishers, North Holland, N.Y., Lunblad, R. L., et at., eds. (1981).

"NAC-antiproliferative heparin" refers to a mixture of non-fragmented glycosaminoglycan chains obtained by treating commercially available heparin with periodate as described herein, which mixture substantially lacks anticoagulant activity but inhibits the proliferation of smooth muscle cells.

Inhibition of Angiogenesis

A key property of the invention sulfated maltooligosaccharides is that they exhibit significant anti-angiogenic or angiostatic activity. Angiogenesis is the process whereby new blood vessels are produced. It is a process that may be associated with certain diseases, including arthritis, retinopathies, and the growth and metastasis of tumors. See, Mitchell and Wilks, *Annual Reports in Medicinal Chemistry* (Academic Press 1992) 27: 139–148; Chapter 15.

Compositions that stimulate or inhibit angiogenesis can be identified using several assays known in the art. The chick chorioallantoic membrane (CAM) assay is commonly used. Using the CAM assay, certain heparinoids inhibit angiogenesis when administered with certain steroids. Folkman and Ingber, *Ann, Surg.* (1987) 206:374. Folkman et at., *Science* (1983) 221:719.

The invention compositions described herein also exhibit anti-angiogenic activity in the CAM assay, and thus can be used to treat angiogenic based diseases. As mentioned above, one such disease is cancer. Thus, while Applicants do not intend to be held to any one specific mechanism of action to explain the biological activity of their compositions, the anti-angiogenic activity of the highly sulfated maltooligosaccharides would account for, at least in part, their anti-cancer activity.

Inhibition of Heparanase

The metastatic spread of tumor cells throughout the body is thought to be facilitated by enzymes secreted by tumor cells that degrade components of the basement membrane, thereby allowing tumor cells to disseminate via the circulation. One such enzyme is endo-β-D-glucuronidase, or heparanase, which degrades heparan sulfate glycosaminoglycans. Heparan sulfate is a prominent component of parenchymal cell basement membranes. The highly sulfated maltooligosaccharides of the instant invention exhibits significant heparanase inhibitory activity as revealed using standard assays. Thus, cancer, and other diseases that have as one element unwanted heparanase activity can be beneficially treated with the compositions of the invention.

Inhibition of bFGF Activity

Basic fibroblast growth factor (bFGF) is a small, heparin-binding polypeptide growth factor which is mitogenic for a variety of cell types of meso- and neuroectodermal origin. The mitogenic activity of bFGF is believed to derive from its specific interaction with one or more high affinity transmembrane receptors in the tyrosine kinase gene family.

Basic FGF is also known to ihteract with cell surface and extracellular matrix heparan sulfate proteoglycan (HSPG), and such molecules are often referred to as "low affinity" receptors. The protein also binds heparin quite strongly in vitro, and advantage of this is taken in the routine purification of bFGF on affinity columns of immobilized heparin. More recently, several studies have provided evidence that heparin or the heparan sulfate (HS) chains of HSPG may in fact be a cofactor that promotes or enhances the binding of bFGF to its high affinity receptors.

The bFGF binding properties of certain heparins or heparin like molecules are described by Ishihara, M., et at., *Anal Biochem* (1992) 202:310–315.

The capacity of the invention compositions to bind to bFGF and inhibit bFGF dependent cell growth can be shown using certain assays. Assays for measuring the effect of heparinoids on bFGF are known in the art. A cell based competitive binding assay is described by Ishihara, M., et al., *Anal Biochem* (1992).202:310–315. The assay is based on the observation that bFGF brads to a lymphoblastoid cell line, transfected with hamster syndecan (RO-12 UC cells), and that this interaction can be inhibited by compositions that bind to bFGF.

A key aspect of the invention compositions is that the inhibition of bFGF-dependent cell growth is dependent on the degree of sulfation of the maltooligosaccharide compositions, the highly sulfated compositions described herein being the most effective.

Platelet Inhibition

Heparin is known to have an anti-thrombotic effect, and at least in part this is a result of heparin's capacity to inhibit platelet aggregation. Interference with platelet aggregation causes a significant bleeding liability in some patients. Certain NAC heparins exhibit both non-anhcoagulant activity and inhibit platelet aggregation. See, for example, co-owned U.S. Patent application, Ser. No. 753,299, filed Sep. 3, 1991, or PCT Patent application Ser. No. 92/02516; filed Mar. 27, 1992. The preferred compositions similar to heparin, of the instant invention inhibit platelet aggregation.

The following examples are intended to illustrate but not to limit the invention. For example, those skilled in the art would know that there are materials and methods that can be substituted for those described below, and still come within the scope of what is detailed in the Examples.

EXAMPLES

Example 1

Effect of Sulfation of Maltooligosaccharides on Cell Binding and Proliferation

To study the effect of the degree of sulfation on the biological properties of maltooligosaccharides, maltohexaose was sulfated with 6, 12, and 18 moles per mole of maltohexaose with sulfur trioxide pyridine complex to give Compositions 1, 2, and 3 in Table 1, respectively. Composition 4, the most highly sulfated composition, was generated using an excess (2 moles/hydroxyl group) of the sulfur trioxide pyridine complex in DMF.

The average degree of sulfation of the products was deduced from the data of elementary analysis. Because of the hygroscopic nature of the products the carbon/sulfur ratio was used instead of the sulfur content.

More specifically, sulfation was carded out as follows: Compositions 1, 2 and 3 were made in three parallel experiments. To a solution of maltohexaose (0.198 g) in N,N-dimethylformamide (10 mL) sulfur trioxide pyridine complex (0.191 g (Experiment 1), 0.382 g (Experiment 2), and 0.573 g (Experiment 3), respectively) was added. The mixtures were stirred at room temperature for two days. The pH was adjusted to 9 with 1M NaOH, and the mixtures were evaporated to dryness under reduced pressure. The crude products were desalted on a Biogel P-2 column with 0.5M $NH_4HCO_3$ as eluents, then were further purified by passing through a column of SP Sephadex C25 (Na+) ion-exchange gel with water as eluent to give 0.110 g (Experiment 1), 0.187 g (Experiment 2), and 0.350 g (Experiment 3) product, respectively. Compositions 1, 2 and 3 were produced in Experiments 1, 2 and 3, respectively.

Composition 4, highly sulfated maltohexaose was made as follows: Maltohexaose (0.5 g) in N,N-dimethylformamide (20 mL) was treated with sulfur trioxide pyridine complex (3.21 g) and the mixture was stirred at room temperature for 2 days. The pH was adjusted to 9 with 1M NaOH, and the product was precipitated by the addition of ethanol. The crude product was filtered and was desalted on a Biogel P-2 column with 0.5M $NH_4HCO_3$, then passed through a column of AG 50W-X8 (Na+) ion-exchange resin with water, to give 1.24 g material after lyophilization. The results are summarized in Table 1.

TABLE 1

Degree of Substitution of Sulfated Maltohexaose

| Composition | C/S Ratio Found | C/S Ratio Calculated | Degree of Sulfation | # OH Groups in Parent Composition |
|---|---|---|---|---|
| 1 | 6.12 | 6.74 | 2 | 2 |
| 2 | 2.37 | 2.25 | 6 | 20 |
| 3 | 1.20 | 1.22 | 11 | 20 |
| 4 | 0.90 | 0.90 | 15 | 20 |

The effect of Compositions 1, 2, 3 and 4 on the binding of RO-12 UC cells to bFGF coated micro-titer wells was determined as described by Ishihara, M., et al., Anal Biochem (1992) 202:310–315. Bound cells are readily quantitated as total protein. Heparin which inhibits RO-12 UC cell binding was run as a positive control.

The assay was run as follows: Fifty microliters of 10 ug/ml human recombinant bFGF was added to wells of a 96-well tissue culture plate and incubated overnight at 4° C. The wells were aspirated with PBS to remove any unbound bFGF, rinsed twice with PBS, and subsequently incubated with PBS containing 5% (v/v) fetal bovine serum for 1 hour at room temperature. RO-12 UC cells were suspended at a density of $3 \times 10^6$ cells/ml in PBS containing 5% fetal bovine serum. To this mixture was added the desired amount of sulfated composition, or heparin. They were made up in PBS plus 2.5% fetal bovine serum. A control was also run, containing only PBS plus 2.5% fetal bovine serum. Next, 100 ul of the cell suspension was immediately added to the microtiter wells, and incubated for 5 minutes, after which the wells were washed 3 times with PBS. Finally, the amount of cell protein bound to the wells was determined by dissolving the bound cells in 20 ul of 5% SDS and measuring the protein concentration of the cell lysates. BSA was used as the standard.

The results are shown in FIG. 1. It is apparent that the more highly sulfated the maltohexaose is, the greater its ability to block RO-12 UC cell adhesion to bFGF-coated wells.

Figure 2:
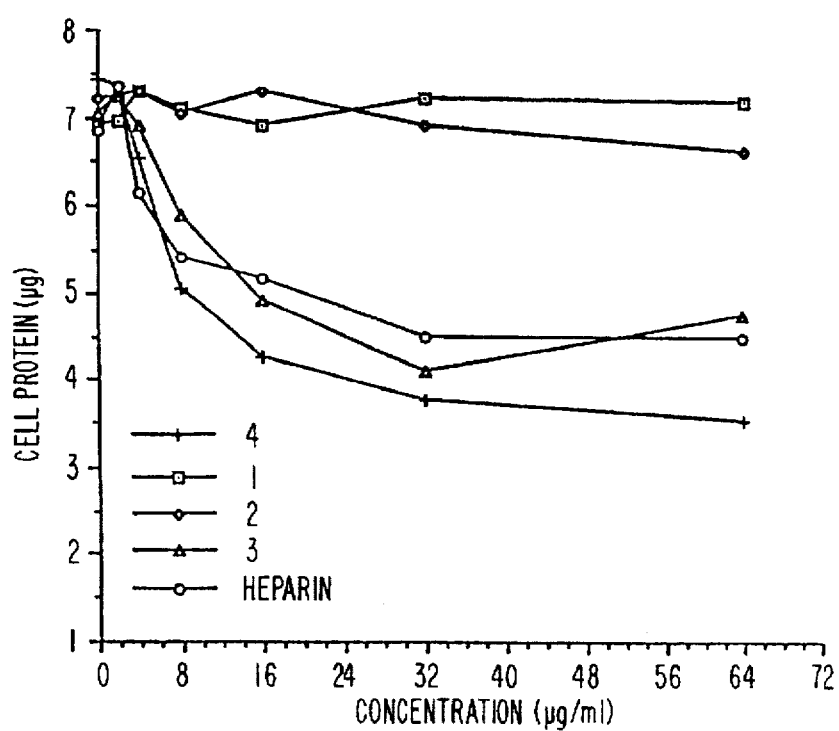
FIG. 2 shows the effects of the degree of sulfation of certain maltooligosaccharides on the inhibition of adrenocortical endothelial cell proliferation.

To extend the effects seen with RO-12 UC cells, a second experiment was conducted. The capacity of the sulfated maltohexaoses to inhibit the proliferation of a bFGF-dependent adrenocortical endothelial (ACE) cell line was determined. This cell line (provided by D. Gospodarowicz, UCSF) requires either aFGF or bFGF for a proliferative response. Cells were seeded at low density in microtiter wells in the presence of 2 ng/ml bFGF, and growth was determined as total protein after four days in the presence of the sulfated maltohexaoses. The results are shown in FIG. 2. Again, the more highly sulfated maltohexaose compositions exhibited the highest anti-proliferative activities.

Example 2

Synthesis of Sulfated Maltotetraose and Biological Activity

Maltotetraose may be purchased commercially from Sigma Corporation or can be produced enzymatically using the procedure of Ratanakhanockchal et at. See, Applied and Environmental Microbiology: vol. 58, no. 8, pages 2490–2494. Maltotetraose is sulfated as follows.

Maltotetraose (0.50 g) in N,N-dimethylformamide (20 mL) was treated with sulfur trioxide pyridine complex (3.34 g) at room temperature. A brownish syrup precipitated in about 15 minutes. The mixture was stirred for 2 days at room temperature then was cooled to 0° C. The pH was adjusted to approximately 9 with 1N NaOH. The product was precipitated with ethanol, and the solid was filtered and washed with ethanol. The crude product (3.22 g) was desalted on a Biogel P-2 column with 0.5M $NH_4HCO_3$. Lyophilization of the carbohydrate containing fractions gave 1.44 g off-white solid. This material was passed through a column of AG W50-X8 (Na+) ion-exchange resin using water as eluent to give 1.51 g product. The degree of sulfation of the product, denoted Composition 5, is shown in Table 2.

TABLE 2

Degree of Substitution of Maltotetraose

| Composition | C/S Ratio Found | C/S Ratio Calculated | Degree of Sulfation | # OH Groups in Parent Composition |
|---|---|---|---|---|
| 5 | 0.69 | 0.69 | 13 | 14 |

Figure 3:
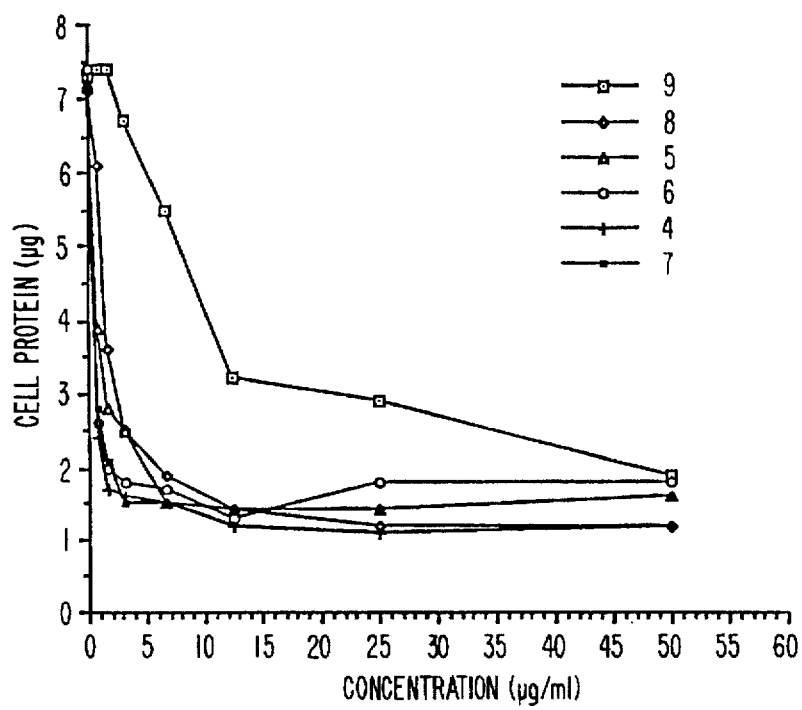
FIG. 3 shows the inhibition of binding of RO-12 UC cells to bFGF coated microtiler wells as a function of the size of certain sulfated maltooligosaccharides.
Figure 4:
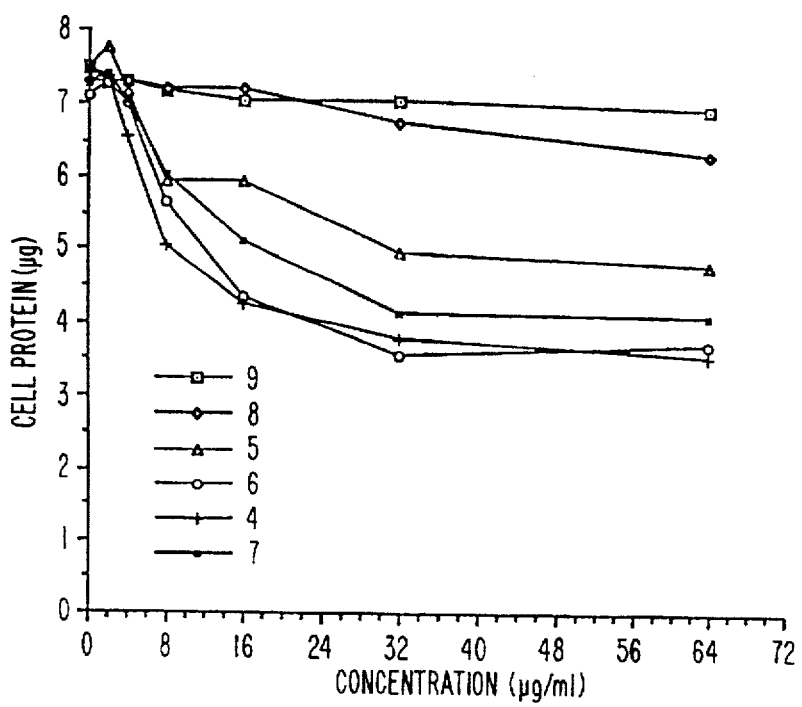
FIG. 4 shows the inhibition of adrenocortical endothelial cell proliferation as a function of the size of certain sulfated maltooligosaccharides.

The capacity of sulfated maltotetraose to inhibit cell binding and cell proliferation was described using the assays set forth in Example 1 and the restfits are shown in FIGS. 3 and 4. It is apparent that this composition has significant activity in both assays.

Example 3

Synthesis of Highly Sulfated Maltopentaose and Maltoheptaose

Maltopentaose and maltoheptaose were obtained from Sigma Corporation, and sulfated using essentially the reaction conditions described for the sulfation of maltotetraose in Example 2. Maltoheptaose can also be prepared by the acetolysis of β-cyclodextrin as described by N. Sakairi et al., J. Chem. Soc. Chem, Commun., (1991) 289. The degree of sulfation of both compositions, maltopentaose and maltoheptaose, is shown in Table 3 as Compositions 6 and 7, respectively.

TABLE 3

Degree of Substitution of Sulfated Maltopentaose/Maltoheptaose and Biological Activities

| Composition | C/S Ratio Found | C/S Ratio Calculated | Degree of Sulfation | # OH Groups in Parent Composition |
|---|---|---|---|---|
| 6 | 1.29 | 1.25 | 9 | 17 |
| 7 | 0.91 | 0.93 | 17 | 23 |

The capacity of highly sulfated maltopentaose and highly sulfated maltoheptaose to inhibit cell binding and cell proliferation was tested using the assays set forth in Example 1.

and the results are shown in FIGS. 3 and 4, respectively. It is apparent that both compositions, similar to highly sulfated maltotetraose, show significant activity in both assays.

Example 4

Synthesis of Highly Sulfated Maltose and Maltotriose and Biological Activities To determine ff the size of highly sulfated maltooligosaccharides is an important factor in regulating cell growth or cell binding, maltose and maltotriose were sulfated and tested in the assays described above.

Maltotriose may be purchased commercially or can be produced enzymatically using the procedure of RatanakhanockchaI et al. See Applied and Environmental Microbiology:58, no. 8, pages 2490–2494. Maltotriose was sulfated as follows. Maltotriose and maltose were sulfated using essentially the reaction conditions described for maltotetraose. In the case of maltose, after adjusting the pH to 9 the product was not collected by precipitation with ethanol, but by concentrating the reaction mixture under reduced pressure. The degree of substitution of the Composition 8 is shown in Table 4.

TABLE 4

| | Degree of Substitution of Maltotriose | | |
|---|---|---|---|
| | C/S Ratio | Degree of | # OH Groups |
| Composition | Found | Calculated | Sulfation | in Parent Composition |
| 8 | 0.69 | 0.67 | 10 | 11 |

The capacity of sulfated maltotriose to inhibit cell binding and cell proliferation was tested using the assays set forth in Example 1 and the results are shown in FIGS. 3 and 4, respectively. It is apparent that this composition shows little or no activity in both assays. Maltose was sulfated to a high degree and tested in the cell binding and cell proliferation assays described in Example 1. The degree of sulfation is shown in Table 5, and the biological data are presented in FIGS. 3 and 4, respectively. Note that this composition, denoted Composition 9 in the table, has little or no activity relative to the highly sulfated maltotetraose composition, and the other larger highly sulfated oligosaccharides shown in the figures.

TABLE 5

| | Degree of Substitution of Maltose | | |
|---|---|---|---|
| | C/S Ratio | Degree of | # OH Groups |
| Composition | Found | Calculated | Sulfation | in Parent Composition |
| 9 | 0.64 | 0.64 | 7 | 8 |

Based on these results shown here and in Examples 1–3, it is apparent that both the size and degree of sulfation of maltooligosaccharides affect cell binding and cell proliferation. Highly sulfated maltooligosaccharides where $n \geq 4$ are the most effective in both assays. In contrast, highly sulfated maltotriose and highly sulfated maltose are less active in both assays.

Example 5

Effects of Highly Sulfated Maltotetraose on Tumor Growth

Experiments were conducted to test the efficacy of highly sulfated maltotetraose, Composition 5, Table 2, on tumor growth in an animal model system, the nude mouse. The growth of human tumors in the nude mouse has clinical relevance to the growth of tumors in humans.

Three human tumor cell lines were utilized, the mammary adenocarcinoma, MDA231, the pancreatic tumor cell line, CAPAN-2, and the prostatic adenocarcinoma cell line, PC-3. All cell lines are available from the American Type Culture Collection, and grow aggressively in nude mice. The experiments were conducted as follows: female, 15–20 gram nude mice, in groups of ten, were inoculated subcutaneously with $3-5 \times 10^6$ viable MDA231, CAPAN-2, or PC-3 cells in 0.1 ml PBS. The cells were grown in standard DMEM tissue culture media supplemented with 10% fetal calf serum in a humidified 5% CO2 incubator at 37° C. The cells were harvested with trypsin-EDTA, washed 2× with PBS, resuspended at a concentration of $3-5 \times 10^7$ cells/ml, and placed on ice prior to injection.

On a daily basis, the mice were subcutaneously injected with 100 mg/kg of highly sulfated maltotetraose made up in PBS, and produced as described in Example 2. The composition was filter sterilized with a 0.2 um Gelman filter unit.

Tumor volume was determined using the following formula:

$$\text{Tumor Volume} = \frac{\text{Length} \times \text{Width}^2}{2}$$

Figure 5:
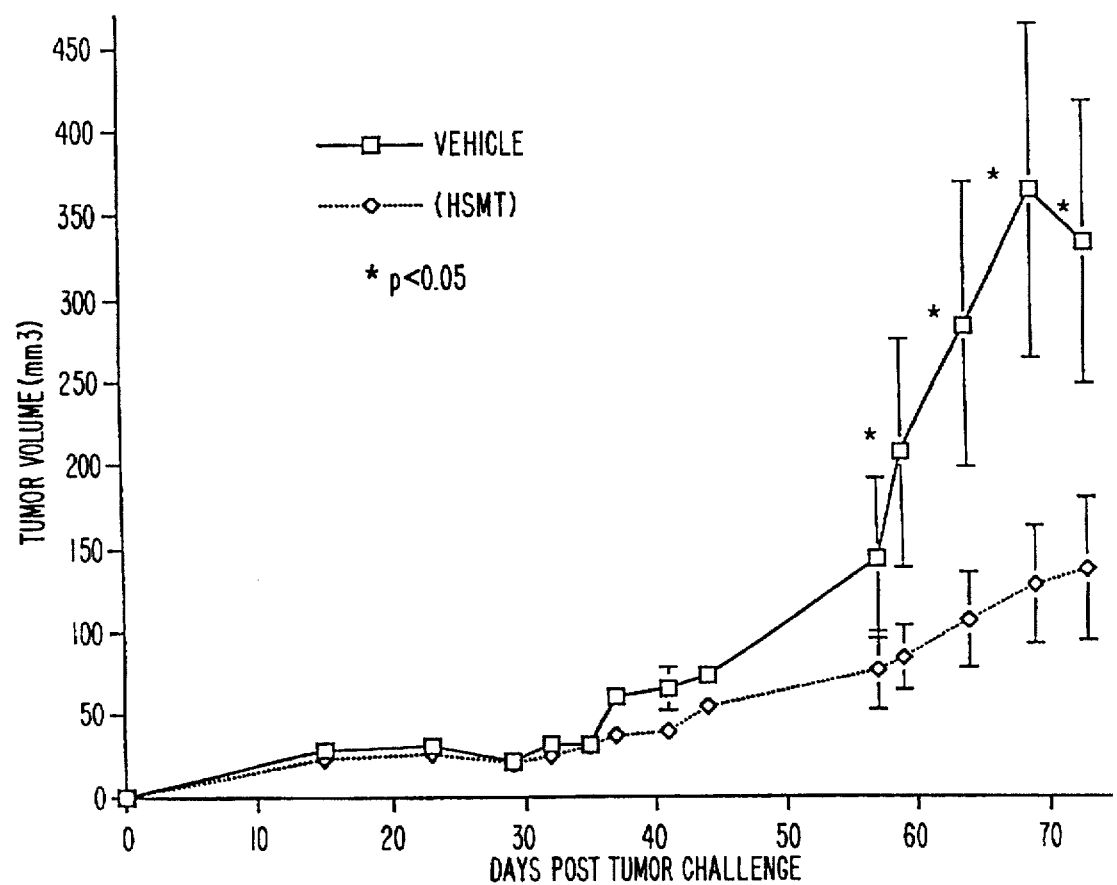
FIG. 5 shows the effects of highly sulfated maltotetraose on the growth of the tumor cell line MDA-23 1 in nude mice.

The effects of sulfated maltotetraose on MDA231 tumor growth are shown in FIG. 5. Control mice were injected with PBS vehicle only. Experimental and control mice were injected twice daily with 0.05 ml of the appropriate solution starting on days 0–40 post tumor challenge. From days 41–70 the animals were dosed once daily with 100 mg/kg/day in a volume of 0.1 ml per injection, and tumor volume measured at defined times using standard methods.

Referring to FIG. 5, it is apparent that tumor growth is significantly inhibited. Inhibition is first apparent at about days 36–37, and is dramatic by days 68–69. Note that from about day 59 until the end of the experiment (day 70), inhibition was significant at p values of <0.05. The tumor volume at days 68–69 in control and sulfated maltotetraose treated animals is about 375 mm$^3$ and 125 mm$^3$, respectively.

Figure 6:
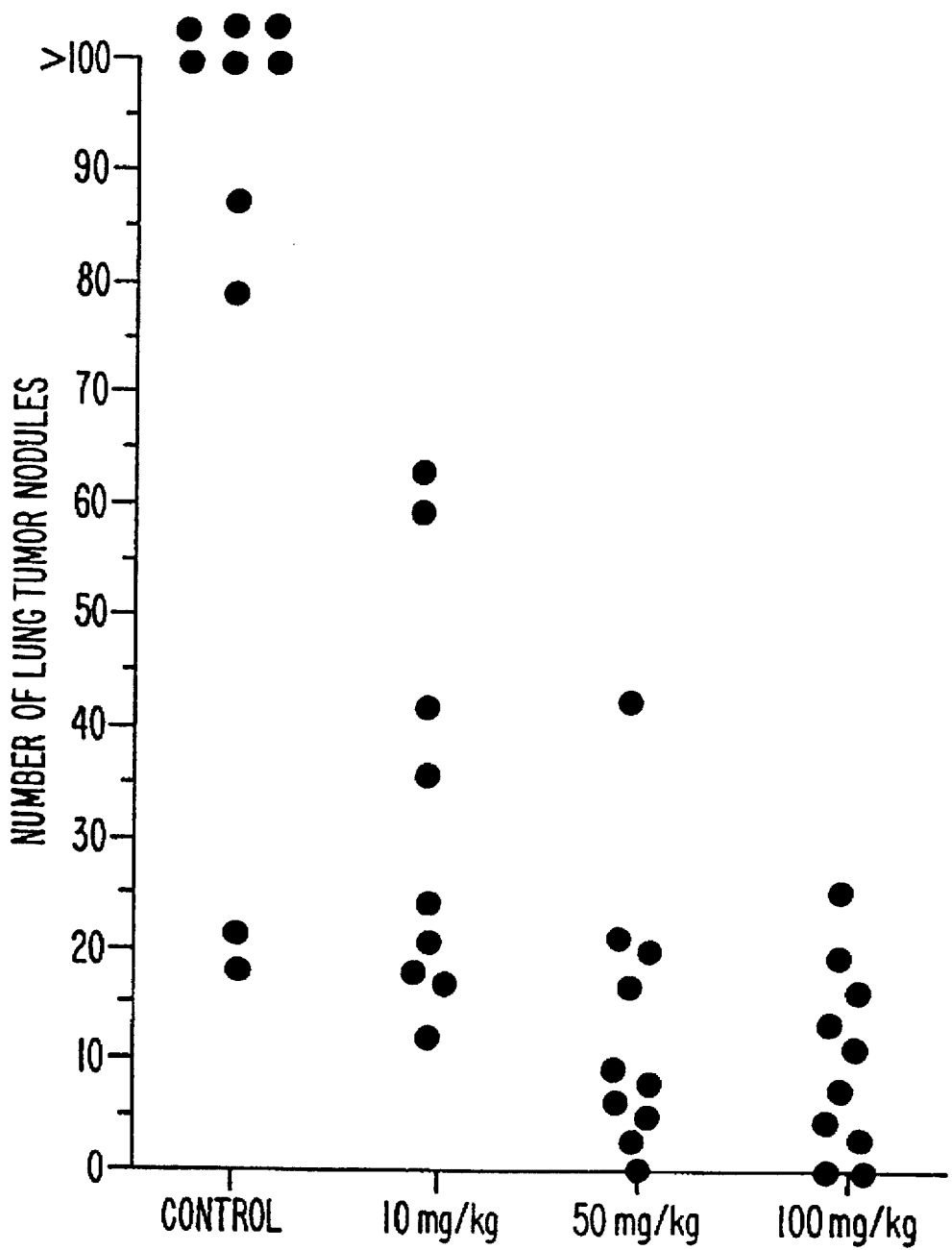
FIG. 6 shows the effects of highly sulfated maltotetraose on CAPAN-2 tumor cell growth in nude mice.

The effects of highly satfated maltotetraose on CAPAN-2 tumor cell growth were determined using the materials and methods set forth above with the following exceptions. Two groups of 20 female nude mice were used for the experimental and control groups, and the animals were dosed once daily starting on day 0 of tumor challenge. The results are shown in FIG. 6. It is apparent that this composition also significantly inhibits tumor growth. Inhibition is observed at days 20–34 and 41–48. The experiment was run for 52 days.

Finally, the effects of highly sulfated maltotetraose on the human prostatic adenocarcinoma line, PC-3, was determined. This cell line is also available from the American Type Culture Collection. The materials and methods described above were similarly used here with the following exceptions. The composition was administered subcutaneously in a single dose of 80 mg/kg/day in a volume of 0.05 ml per dose Animals were dosed beginning 24 hours after tumor challenge. $5 \times 10^6$ PC-3 cells were injected in a volume of 0.1 ml subcutaneously in the anterior dorsal region (12 animals/treatment group).

Figure 7:
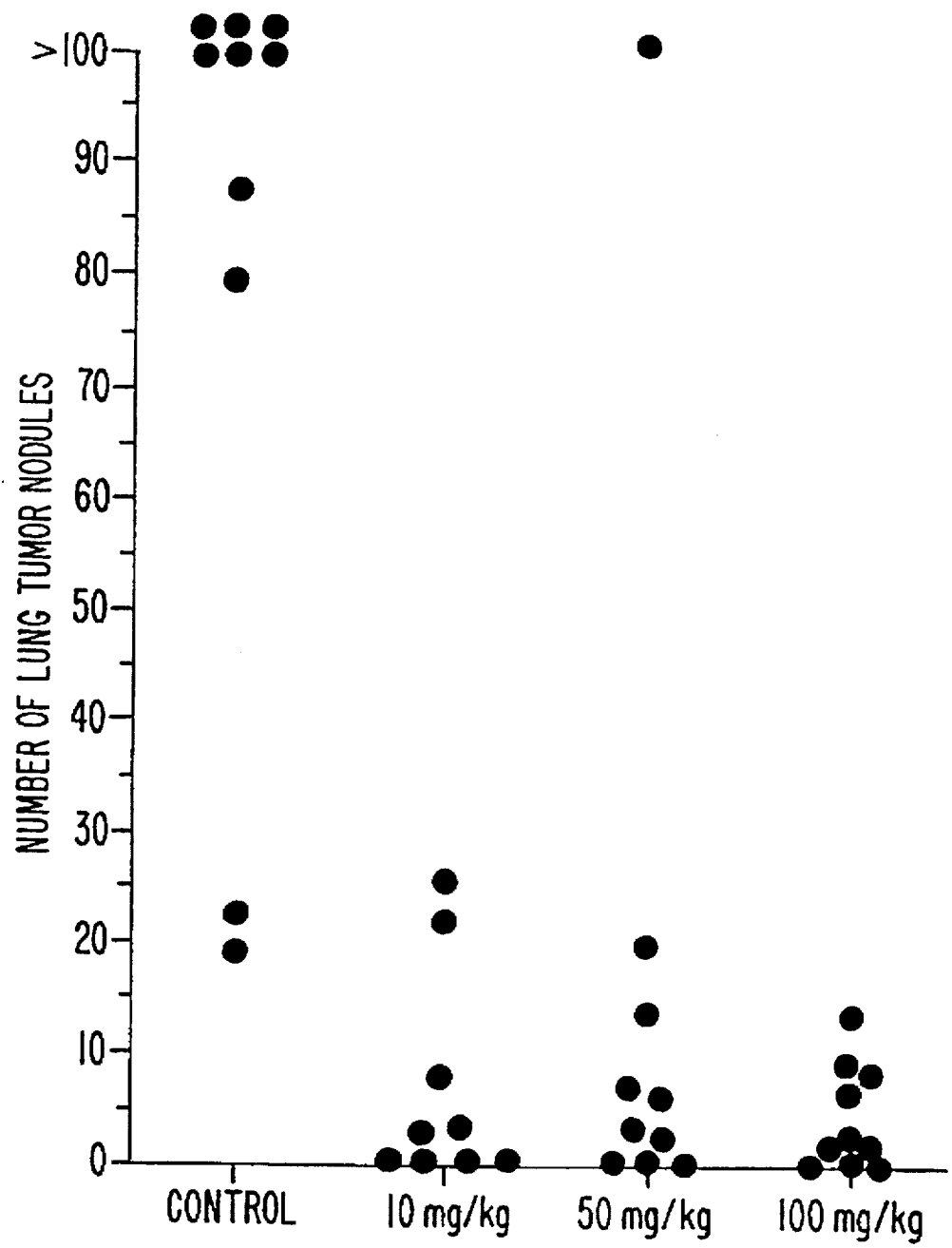
FIG. 7 shows the effects of highly sulfated maltotetraose on the growth of the tumor cell line, PC-3, in nude mice.

The experiment was conducted for 23 days. The results are shown in FIG. 7. The highly sulfated maltotetraose composition inhibited PC-3 cell growth at all the time points tested. Note that at days 15, 19, and 21 growth inhibition was significant at p values of p=0.06, 0.058, and 0.093, respectively.

Example 6

Inhibition of Smooth Muscle Cell Growth

Maltotetraose, maltopentaose and maltohexaose were sulfated as described in Examples 1–3, and assayed for their effects on smooth muscle cell proliferation using a standard assay for this activity. A convenient assay, in detail, is as follows:

Solutions to be tested are made up in DMEM medium containing 10% fetal calf serum and penicillin/streptomycin. Bovine smooth muscle cells (SMC) are isolated from bovine aorta by the method of Ross, R., *J Cell Biol* (1971) 172–186. SMC from passage 3–10 are plated at 350–700 cells per well in 96-well microtiter plates in the medium above and allowed to attach for 2–4 hr. The complete medium is then replaced with DMEM supplemented with 0.1% fetal calf serum, and the cells are incubated for an additional period of about 24 to 72 hr to arrest cell growth. The low-serum medium is then replaced with complete medium containing the test samples. The sulfated maltose oligosaccharides of the invention were added to the medium to make final concentrations as shown in the figures. The effects of heparin at the same concentrations were also determined. The results are plotted as the per cent of heparin inhibition where the concentration of heparin that gave 100% inhibition of SMC proliferation was 150 ug/ml.

The cells are allowed to grow for up to 7 days with replicate plates sampled at regular intervals. Cell number is determined by removing the medium and washing the cells with phosphate-buffered saline, adding 75–150 ul lysis buffer, and assaying for lactate dehydrogenase (LDH) activity, as described by Brandley, B., et at., *J Biol Chem* (1987) 262:6431. The activity of LDH is proportional to cell number.

Figure 8:
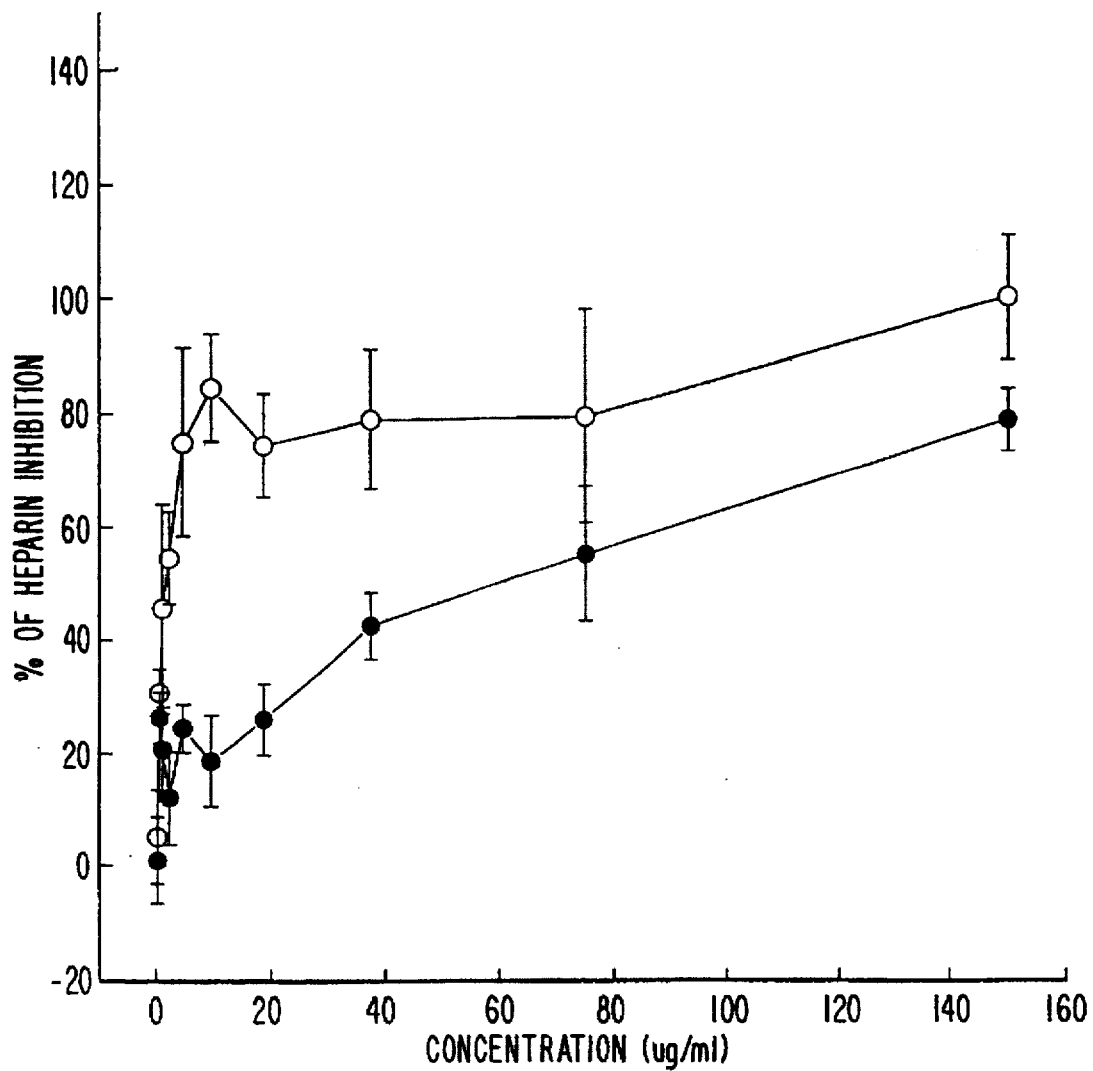
FIG. 8 shows the inhibitory effects of highly sulfated maltotetraose on smooth muscle cell growth. The effects are depicted relative to porcine mucosal heparin.
Figure 9:
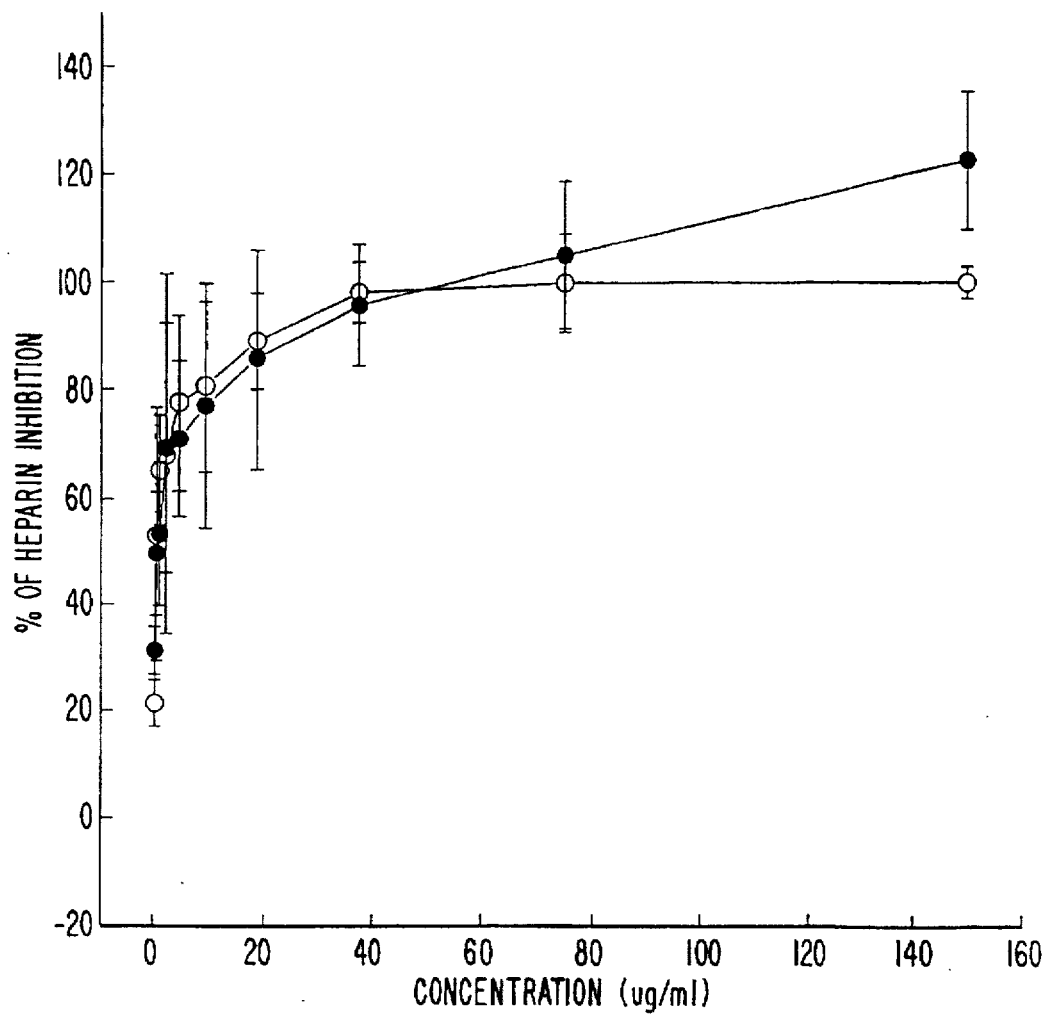
FIG. 9 shows the inhibitory effects of highly sulfated maltopentaose on smooth muscle cell growth. The effects are depicted relative to porcine mucosal heparin.
Figure 10:
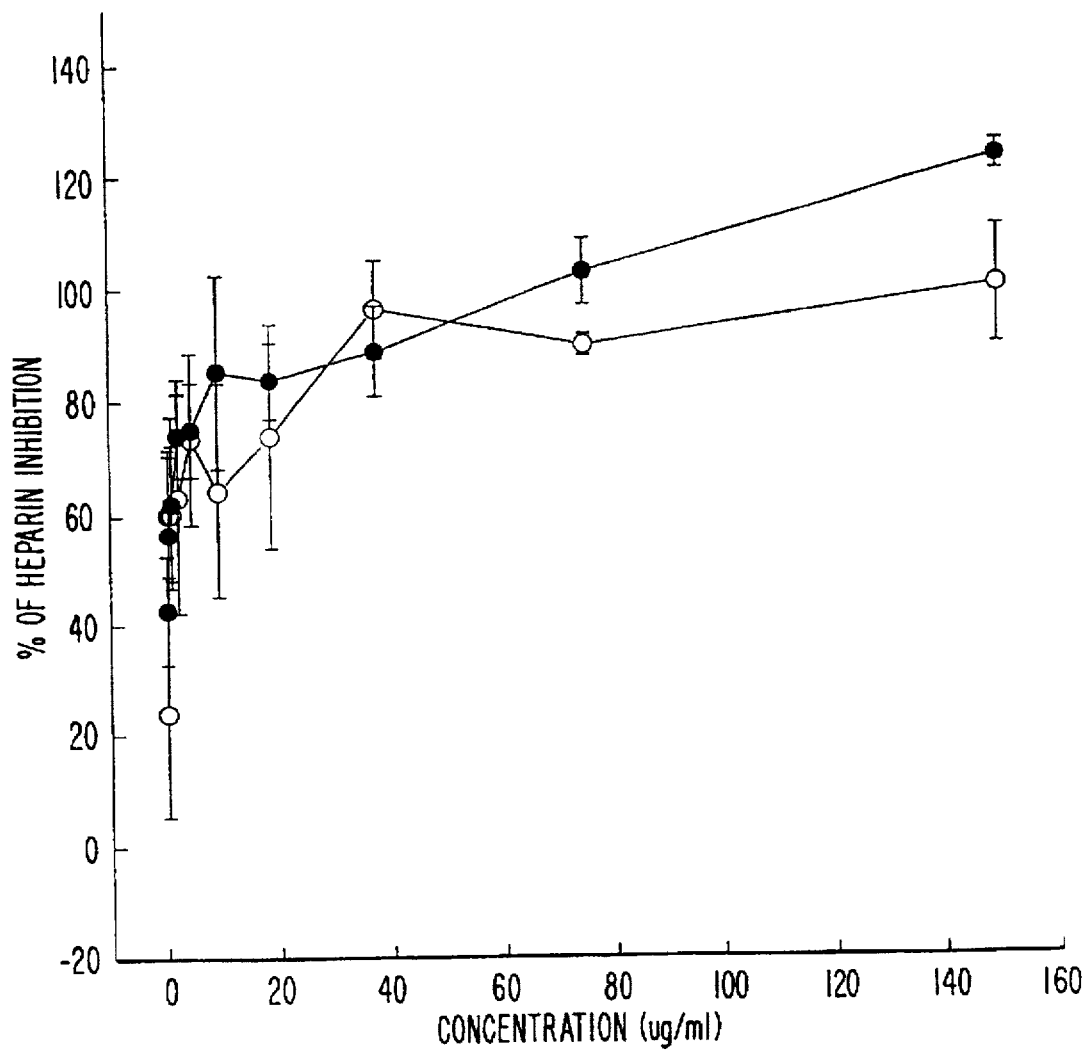
FIG. 10 shows the inhibitory effects of highly sulfated maltohexaose on smooth muscle cell growth. The effects are depicted relative to porcine mucosal heparin.

The results are shown in FIGS. 8–10. FIG. 8 shows the anti-proliferative activity of highly sulfated maltotetraose. This composition exhibits significant anti-proliferative effects, although not as great as heparin. With respect to heparin, about 50% inhibition is observed at about 60 ug/ml.

FIG. 9 shows the anti-proliferative activity of highly sulfated maltopentaose. This composition is more effective in inhibiting SMC proliferation than the smaller-sized sulfated maltotetraose. Indeed, 100% inhibition of SMC growth is observed at about 50 ug/ml. In contrast, one hundred per cent inhibition was not observed for highly sulfated maltotetraose at a concentration of 150 ug/ml.

FIG. 10 shows the anti-proliferative activity of highly sulfated maltohexaose. This composition shows similar efficacy in comparison to highly sulfated maltopentaose. These date show that highly sulfated maltooligosaccharides of the invention are inhibitors of SMC growth, and thus, can be beneficially applied for the treatment of diseases where SMC growth is sought to be controlled or eliminated.

Example 7

Angiostatic Activity

Compositions that stimulate or inhibit angiogenesis can be identified using several assays known in the art. Highly sulfated maltotetraose, Composition 5, Table 2, was tested for angiogenesis activity using the chicken chorioallantoic membrane (CAM) assay. The assay was performed as described by Castellot et. at., *J. of Cellular Physiology* (1986) 127: 323–329, with the exception that samples were evaluated for their efficacy to inhibit neovascularization. Carboxy methyl cellulose pellets containing 50 ug of hydrocortisone, or hydrocortisone plus different amounts of highly sulfated maltotetraose were incubated on the CAM for 3–4 days before scoring the results. Highly sulfated maltotetraose was produced as described in Example 2. Angiostatic activity is defined as a partial clearing or an avascular zone around the pellet. In all cases, pellets at each maltooligosaccharide concentration contained 50 ug of hydrocortisone. The number in the Table is the number of embryos scored that exhibited no effect, a partial clearing (+), or an avascular zone (++). Table 6 shows the results.

It is apparent that the sulfated composition exhibits angiostatic activity. At low concentrations (eg. 3 and 6 ug/mL), the composition is slightly better at inhibiting the formation of new blood vessels than the buffer control, or hydrocortisone alone. At the higher concentrations, 12.5, 25, and 50 ug/ml, increase in partial clearing areas and avascular zone are observed.

TABLE 6

Angiostatic Activity of Highly Sulfated Maltotetraose (HSM)

| SAMPLE | NO EFFECT | + | ++ |
|---|---|---|---|
| Buffer Control | 39 | 0 | 0 |
| Hydrocortisone 50 ug/pellet | 27 | 2 | 0 |
| Composition 4 + Hydrocortisone 50 ug/pellet | 6 | 2 | 4 |
| 25 | 9 | 11 | 2 |
| 12.5 | 11 | 10 | 3 |
| 6 | 16 | 4 | 0 |
| 3 | 11 | 1 | 0 |

Scoring done at 24 hr
Pellets = 0.5% aqueous methylcellulose
Buffer control - ddH$_2$O
HSM alone was inactive

Example 8

Inhibition of Heparanase

Highly sulfated maltotetraose, Composition 5, Table 2, maltoheptaose and maltose were tested for heparanase inhibitory activity using heparanase from a rat hepatoma cell line. The cell line is described by Gerschenson, et al., *Science* (1970) 170: 859–861. Further, their inhibitory activities were compared to porcine mucosal heparin. The procedures for isolating heparanase from hepatoma cells, and the methods for assaying the activity of the enzyme are known by those skilled in the art. The following procedures and materials were used. Confluent rat hepatoma cell cultures were grown in standard cell culture flasks, and washed 3 times with 10 ml of a 50 mM Hepes solution containing 0.25M sucrose and 0.14M NaCl, pH 7.4. Next, 1 ml of a 50 mM MES buffer, pH 5.2, containing 0.14M NaCl, 6 mM sodium azide, and certain protease inhibitors was added and the cells removed from the flask using a disposable cell scraper. The following protease inhibitors were present in the MES buffer: 0.2 ug/ml aprotinin, 0.5 ug/ml leupeptin, 100 ug/ml soybean trypsin inhibitor, 1 mM PMSF, 2 mM EDTA (sodium salt), and 15 mM D-saccharic acid 1,4 lactone (exoglucuronidase inhibitor).

The cells were added to a 7 ml Dounce homogenizer, freezed/thawed 3 times in an ethanol/dry ice bath, and homogenized with 15 strokes using a tight pestle. The resulting cell lysates were placed in a 2 ml centrifuge tube and centrifuged at 4° C. for 30 minutes at 16,000×g. The supernatant was removed, and the protein concentration in the supernatant determined using the Macro BCA protein assay. BSA was used as a standard. Heparanase activity was quantified by measuring soluble N-$^3$H-acetylated pancreas heparan sulfate fragments derived from uncleaved N-$^3$H-acetylated pancreas heparan sulfate distinguishable by cetylpyridinium chloride (CPC) precipitation. N-$^3$H-acetylated pancreas heparan sulfate had a weight average molecular weight, or Mw, of about 13,000. The following procedures were used.

$^3$H-acetylated pancreas heparan sulfate (248 ng, 80,000 cpm) in 10 ul of 200 mM MES buffer, pH 5.2, containing 0.14M NaCl was added to 1.5 mL siliconized microcentrifuge tubes. Next, 10 ul of distilled water containing various concentrations of porcine mucosal heparin, or the appropriate highly sulfated maltooligosaccharide, was added. Then, 30 ul of rat hepatoma cell supernatant, isolated as described above, containing 7.5–10 ug of protein in 50mM MES buffer, pH 5.2, containing 0.14M NaCl, 6mM sodium azide and the protease inhibitors described above, is added to siliconized 1.5 ml microcentrifuge tubes. Three to six replicates were run for each concentration of highly sulfated maltotetraose while three replicates were run for each concentration of porcine mucosal heparin. Controls were run to account for background counts. It was previously shown that the highest concentration of inhibitor does not affect precipitation of the intact radiolabeled heparan sulfate substrate.

The enzyme substrate inhibitor mixture was mixed, after which the tubes were incubated at 37° C. for 20 minutes. After 20 minutes, the reaction was stopped by adding to the reaction tubes 150 ul of an aqueous heparin solution (0.33 mg/ml), 200 ul of 100 mM sodium acetate pH 5.5 and 100 ul of CPC (0.6% in water) were then added. Three replicates maintained on ice were run as background controls (0 min.) in which the enzyme was added to the tubes immediately followed by heparin to terminate the reaction. The samples were processed as described for the 20 minute time points. Next, the tubes were vortexed, incubated for 60 minutes at room temperature, and then centrifuged for 10 minutes at 4,000×g in a 5415C Eppendoff centrifuge. The supernatant was removed and assayed for $^3$H by liquid scintillation counting.

Values represented are the mean differences between soluble CPM measured at 20 minutes at different heparin or highly sulfated maltotetraose, maltoheptaose, and maltose concentrations and soluble CPM measured at 0 minutes at 0 ug/ml ±the standard deviation of the sum of the 20 and 0 minute variances.

FIG. 11 shows that highly sulfated maltotetraose is approximately one half as effective as porcine mucosal heparin in inhibiting heparanase activity. The IC$_{50}$ values of highly sulfated maltotetraose and porcine mucosal heparin were 9.0 and 4.1 ug/ml, respectively.

Not shown in the figure are the results for maltoheptaose sulfate and maltose sulfate. The former was as active as heparin in the assay, whereas highly sulfated maltose had no activity at greater than 200 ug/ml.

Example 9

Synergistic Effect of Highly Sulfated Maltooligoaaccharides and Chemotherapeutic Drugs in the Treatment of Cancer As discussed above, one mechanism whereby the highly sulfated maltooligosaccharides exert their anticancer effect is by blocking angiogenesis. Thus, experiments would be done to show a synergistic effect of these compositions with chemotherapeutic drugs that are known to be effective for treating cancer.

Such experiments would be done as described in Example 5 using the tumor cell line MDA231, but having an additional test sample consisting of methotrexate. The procedure would be as follows. On a daily basis, mice would be subcutaneously injected with 100 mg/kg of highly sulfated maltotetraose, Composition 5, Table 2, made up in PBS, produced as described in Example 2, with methotrexate. Methotrexate would be used at a concentration of 4 mg/kg. The composition would be filter sterilized with a 0.2 um Gelman filter unit.

Similar to Example 5 tumor volume would be determined using the following formula:

$$\text{Tumor Volume} = \frac{\text{Length} \times \text{Width}^2}{2}$$

Three groups of control mice would be run. They would be injected with either PBS vehicle, 100 mg/kg of highly sulfated maltotetraose in PBS, or 4 mg/kg methotrexate in PBS. Experimental (highly sulfated maltotetraose with methotrexate) and control mice would be injected twice daily with 0.05 ml of the appropriate solution starting on days 0–40 post tumor challenge. From days 41–70 the animals would be dosed once daily with 100mg/kg/day in a volume of 0.1 ml per injection, and tumor volume measured at defined times using standard methods.

The effects of highly sulfated maltotetraose alone on MDA231 tumor growth would be as shown in FIG. 5. That is, tumor growth would be significantly inhibited with inhibition first apparent at about days 36–37, and dramatic inhibition apparent by days 68–69. The tumor volume at days 68–69 in control (PBS) and highly sulfated maltotetraose treated animals would be about 375 mm$^3$ and 125 mm$^3$, respectively.

In the second group of control mice treated with methotrexate alone, similar results would be expected as those observed for mice treated with highly sulfated maltotetraose alone. That is, there would be a significant reduction in tumor volume relative to the PBS control mice; about a 3 fold reduction would be realized.

In contrast, however, mice treated with the combination of highly sulfated maltotetraose and methotrexate would present an average tumor volume less than that observed with either agent alone. Tumor volume would be less than 60 mm$^3$ at about days 68–69.

Example 10

Effects of Highly Sulfated Maltotetraose and Highly Sulfated Maltoheptaose on Human Renal Cell Carcinoma Tumor Growth Experiments were conducted to test the efficacy of highly sulfated maltotetraose (Composition 5, Table 2) and highly sulfated maltoheptaose (Composition 7, Table 3) on human renal cell carcinoma tumor growth in the nude mouse. The materials and methods utilized to carry out the experiments are described by Naito, S., et al., Anticancer Research, volume 8, pages 1163–1168 (1988) and Naito, S., et al., Clin. Expl. Metastasis, volume 7, pages 381–389 (1989).

The experiments were conducted as follows. Nude mice were injected with $10^6$ human renal carcinoma cells in the left renal sub capsule of adult mice (day 0). The human renal carcinoma cell line, SN12, passage number 6, was utilized. Both highly sulfated compositions were used at 10 mg/kg, 50 mg/kg and 100 mg/kg made up in Hanks Balanced Salt Solution. Ten mice were used for each dose. Ten control mice were used that received only Hanks Balanced Salt Solution. Three days (day 3) after mice received tumor cells both control and experimental animals were injected daily for 20 days. All injections were subcutaneous. Two days (day 22) after the administration of highly sulfated compositions, the animals were nephrectomized, and three weeks later sacrificed. The lungs were removed, placed in Bouin's solution, and the number of lung metastases were determined using a dissecting microscope. The results are shown in FIGS. 6 and 7 for highly sulfated maltotetraose and highly sulfated maltoheptaose, respectively.

It is striking that at all concentrations of either highly sulfated composition that there is a reduction in tumor metastases. For both highly sulfated compositions, when the number of metastases in control animals was compared to the number of metastases in the experimental group at all doses (10 mg/kg, 50 mg/kg or 100 mg/kg), p was<0.005.

Having described what the applicants believe their invention to be, a skilled practitioner of this art should not construe the invention to be limited other than by the scope of the appended claims.

What is claimed is:

1. A method for treating an animal for disease wherein said disease is selected from the group consisting of retinopathies and cancer, comprising:

administering to said animal an effective amount of a composition comprising a compound of the formula:

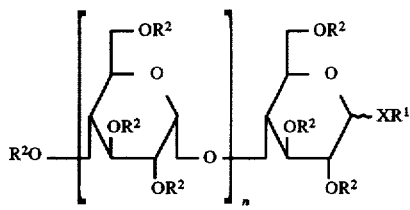

wherein

X represents O or S;

$R^1$ represents an alkyl, aryl, or aralkyl group, a reduced or oxidized glucose unit, $SO_3M$, or H;

each $R^2$ is independently selected from the group consisting of $SO_3M$ group and H;

M represents a biologically acceptable cation; and n represents an integer from 1 to 9; with the proviso that at least 50% of said $R^2$ groups are sulfates.

2. The method of claim 1, wherein n represents an integer from 2 to 7.

3. The method of claim 2, wherein X represents S and $R^1$ is H.

4. The method as described in claim 1 wherein at least 75% of said $R^2$ groups are sulfates in said compound and wherein said compound is selected from the group consisting of sulfated maltotretraose, sulfated maltopentaose, sulfated maltohexaose, and sulfated maltoheptaose.

5. The method as described in claim 4 wherein said cancers are selected from the group consisting of pancreatic, melanoma and adenocarcinoma and said composition is administered with an amount of a chemotherapeutic drug effective for treating cancer.

6. A method for inhibiting heparanase, comprising contacting said heparanase with an effective amount of sulfated maltoligosaccharide wherein at least 50% of the hydroxyl groups are sulfated, selected from the group consisting of sulfated maltotetraose, sulfated maltopentaose, sulfated maltohexaose, and sulfated maltoheptaose.

7. A method for inhibiting the growth of blood vessels from endothelial cells, comprising contacting said endothelial cells with an effective amount of sulfated maltooligosaccharisde wherein at least 50% of the hydroxyl groups are sulfated, selected from the group consisting of sulfated maltotetraose, sulfated maltopentaose, sulfated maltohexaose, and sulfated maltoheptaose.

8. A composition comprising a compound of the formula:

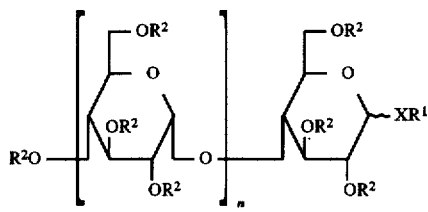

wherein

X represents O or S;

$R^1$ represents an alkyl, aryl, or aralkyl group, a reduced or oxidized glucose unit, $SO_3M$, or H;

each $R^2$ is independently selected from the group consisting of $SO_3M$ group and H;

M represents a biologically acceptable cation; and n represents an integer from 1 to 9; with the proviso that at least 50% of said $R^2$ groups are sulfates;

and a chemotherapeutic drug effective for treating cancer.

9. The method of claim 1, wherein said cancer is a carcinoma.

10. The method as described in claim 9, wherein said carcinoma is renal cell carcinoma.

* * * * *